United States Patent [19]

Gangal et al.

[11] Patent Number: 5,766,216
[45] Date of Patent: Jun. 16, 1998

[54] BAND APPLICATOR FOR APPENDICULAR AND MESO-APPENDICULAR STUMPS

[76] Inventors: Hanamraddi T. Gangal, Dr. Gangal Nursing Home & Research Centre, Hosur, Hubli, India, 580-021; Parag H. Gangal, 5500 LeBeau La., Frisco, Tex. 75034; Madhumalti H. Gangal, Dr. Gangal Nursing Home & Research Centre, Hosur, Hubli, India, 580-021

[21] Appl. No.: 652,698

[22] Filed: May 30, 1996

[51] Int. Cl.⁶ ................................................. A61B 17/10
[52] U.S. Cl. ........................... 606/140; 606/141; 606/151
[58] Field of Search ......................... 606/140, 139, 606/141, 151, 205, 207

[56] References Cited

U.S. PATENT DOCUMENTS

| | | | |
|---|---|---|---|
| 3,870,048 | 3/1975 | Yoon | 128/326 |
| 4,374,523 | 2/1983 | Yoon . | |
| 4,784,137 | 11/1988 | Kulik et al. . | |
| 4,921,423 | 5/1990 | Kesling | 433/3 |
| 4,990,152 | 2/1991 | Yoon | 606/140 |
| 5,026,379 | 6/1991 | Yoon . | |
| 5,217,030 | 6/1993 | Yoon | 128/898 |
| 5,226,908 | 7/1993 | Yoon . | |
| 5,259,366 | 11/1993 | Reydel et al. . | |
| 5,261,918 | 11/1993 | Phillips et al. | 606/140 |
| 5,320,630 | 6/1994 | Ahmed . | |
| 5,382,254 | 1/1995 | McGarry et al. . | |
| 5,398,844 | 3/1995 | Zaslavsky et al. . | |
| 5,433,721 | 7/1995 | Hooven et al. . | |
| 5,476,206 | 12/1995 | Green et al. . | |

*Primary Examiner*—Michael Buiz
*Assistant Examiner*—Tina T. D. Pham
*Attorney, Agent, or Firm*—Daniel V. Thompson

[57] ABSTRACT

A telescopic band applicator for use in applying an elastic band to a stump of tubular tissue includes an outer tubular member, a middle tubular member telescopically received within the outer tubular member, and an inner tubular member telescopically received within the middle tubular member. A plurality of concave prongs at the end of the inner tubular member are adapted and arranged to compress and capture the stump of tissue within the inner cylindrical surface of the middle tubular member for banding.

8 Claims, 4 Drawing Sheets

BAND APPLICATOR FOR APPENDICULAR AND MESO-APPENDICULAR STUMPS

TECHNICAL FIELD

This invention relates generally to surgical devices and instruments, and more particularly, to a laparoscopic instrument for applying bands to stumps of tubular tissue.

BACKGROUND ART

An instrument known as a Yoon-Band Applicator has long been used to apply an elastic occluding ring onto an anatomical tubular structure, such as in sterilization procedures. Said applicator is disclosed in U.S. Pat. No. 4,374,523 to Yoon, now expired. In the conventional use of such an applicator, the size and shape of the tissue involved is well-adapted to receive the elastic ring or band from the applicator.

In appendectomy procedures, however, the appendicular and meso-appendicular stumps are sized such that extreme difficulties in using conventional Yoon-Band Applicators have been experienced. The conventional Yoon-Band Applicator has only two forceps hooks that are constant in width and relatively thin. In using the convention Yoon-Band Applicator, the difficulties encountered included the very poor grip on the appendix, appendicular stump, or meso-appendicular stump. The poor grip was caused by the prongs of the Yoon-Band applicator being too narrow for a proper grip. In addition, because there were only two prongs to the applicator, this caused the appendicular stump and the grasped tissues to bulge and protrude in between the two thin prongs of the application. The bulging and protrusion of the stump between the two prongs made application of the elastic bands extremely difficult. Thus, it is apparent that a need presently exists for a band applicator that is specifically adapted to applying bands to appendicular and meso-appendicular stumps.

SUMMARY OF THE DISCLOSURE

A telescopic band applicator for use in applying an elastic band to a stump of tubular tissue, such as an appendicular or meso-appendicular stump, includes conventional outer, middle and inner tubular members arranged in a telescoping relationship. Instead of the two narrow forceps prongs as in a conventional applicator, a plurality and preferably four concave triangular prongs are provided. The concave prongs are adapted and arranged to compress and capture the stump within the inner cylindrical surface of the middle tubular member.

BRIEF DESCRIPTION OF THE DRAWINGS

A more complete understanding of the invention and its advantages will be apparent from the Detailed Description taken in conjunction with the accompanying Drawings, in which.

DETAILED DESCRIPTION OF THE PREFERRED EMBODIMENT

Figure 1:
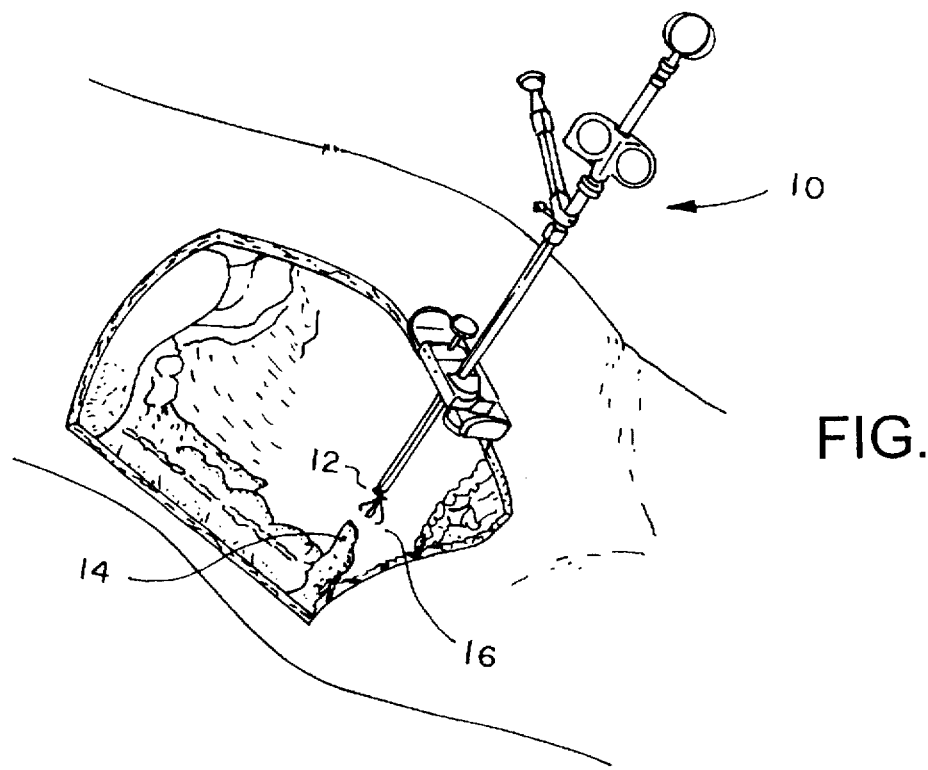
FIGS. 1 and 2 are diagrammatic illustrations of the invention and its preferred environment.
Figure 2:
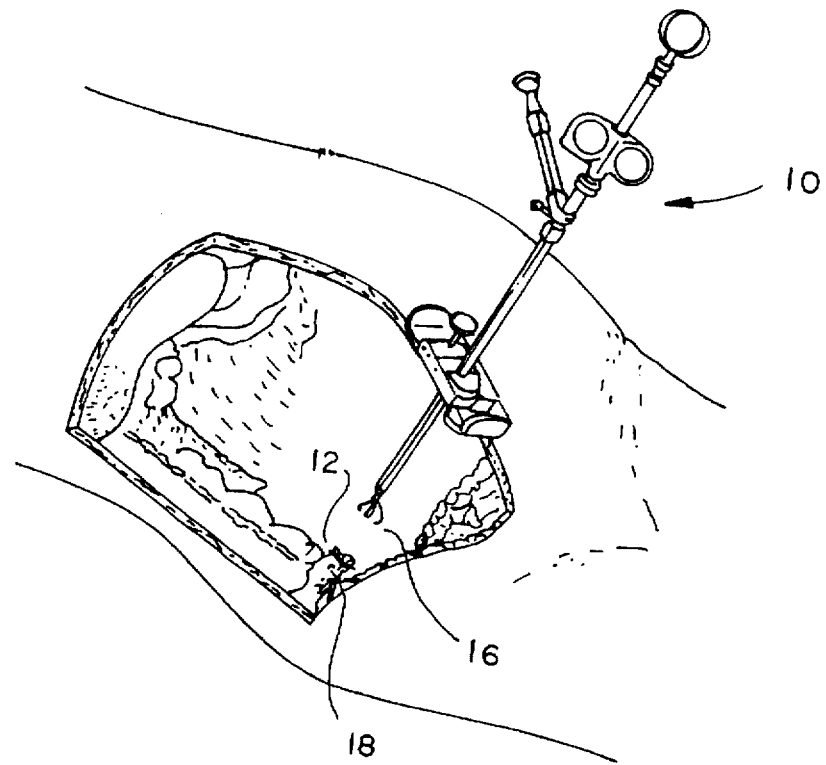
Figure 3:
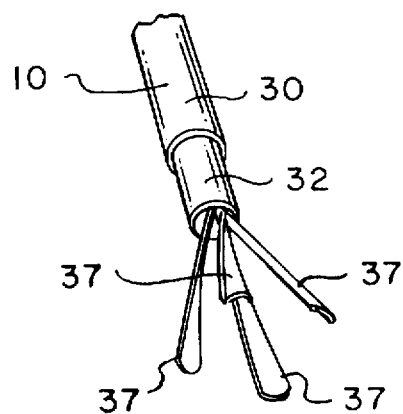
FIG. 3 is a end perspective view of the instrument of the present invention.
Figure 4:
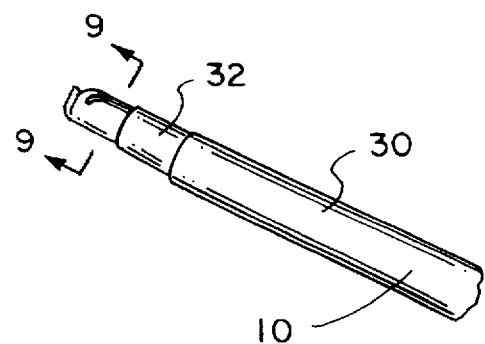
FIG. 4 is a side view of the instrument with the inner tubular member withdrawn into the middle tubular member.
Figure 5:
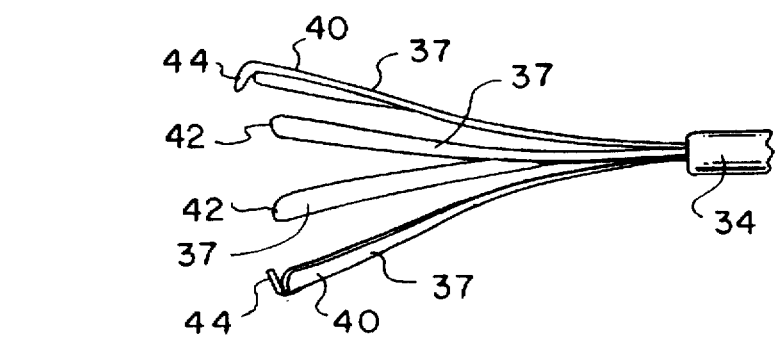
FIG. 5 is a side view of the end of the inner tubular member showing the prongs of the present invention.

Referring initially to FIGS. 1 and 2, where like numerals refer to like and corresponding elements, an instrument 10 is a telescopic band applicator specially adapted for use in applying an elastic band 12 to the stump of an appendix 14, after removal of the appendix. As will be described in detail below, prongs 16 of instrument 10 are specially adapted to perform this function. As shown in FIG. 2, band 12 has been applied to stump 18 as will hereinafter be described.

Figure 6:
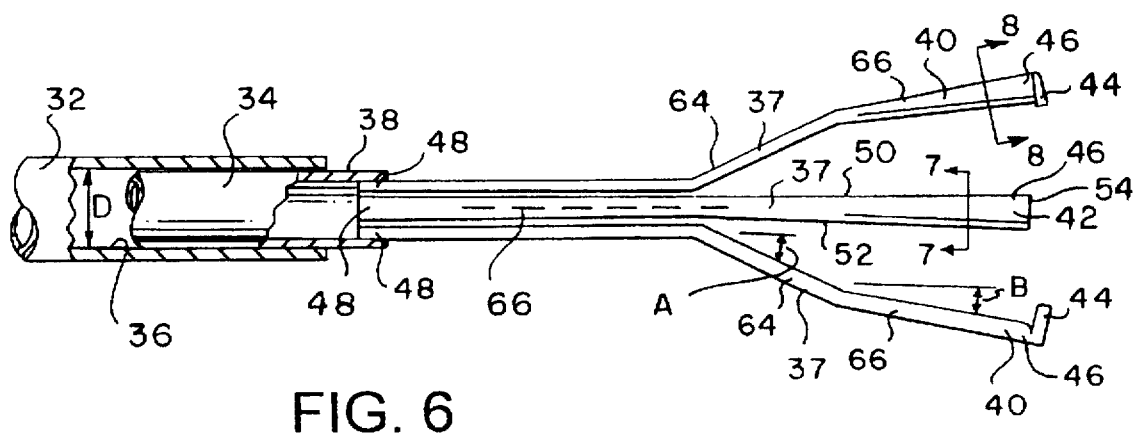
FIG. 6 is a partially broken away side view similar to FIG. 5.

Referring now to FIGS. 3–9, where like numerals indicate like and corresponding elements, instrument 10 includes an outer tubular member 30, a middle tubular member 32, telescopically received within the outer tubular member 30, and an inner tubular member 34, telescopically received within the middle tubular member 32. As best shown in FIG. 6, middle tubular member 32 has a cylindrical inner surface 36.

Four prongs 37 are attached to an end 38 of inner tubular member 34. In the preferred embodiment, prongs 37 are arranged into a first pair of opposed identical prongs 40 and a second pair of opposed identical prongs 42. Each of the first pair of prongs 40 has an inwardly facing forceps hook 44 at the distal end 46 thereof.

Figure 8:
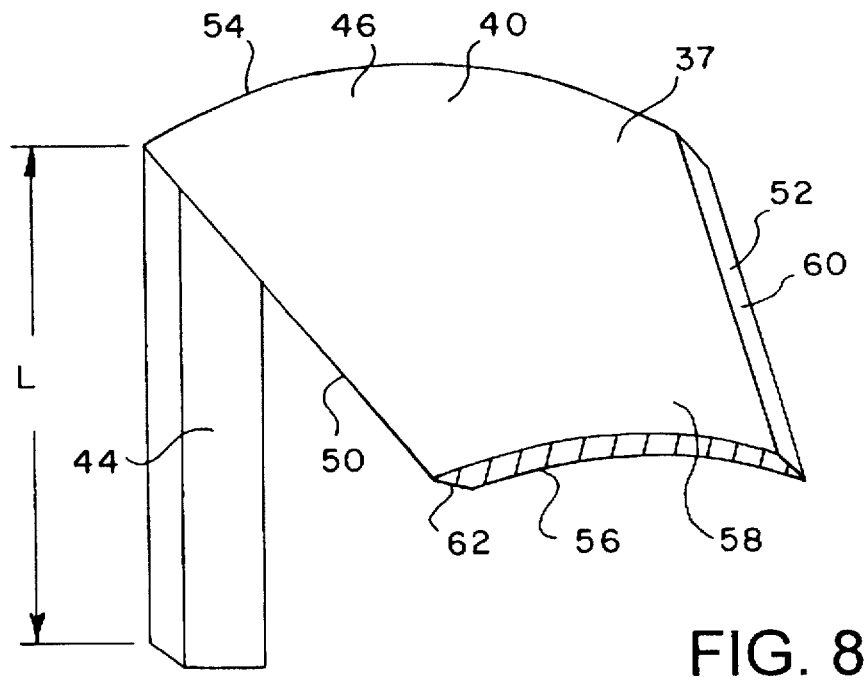
FIG. 8 is a sectional view taken along lines 8—8 of FIG. 6.

Each prong 37 is formed in the shape of an elongated triangle. The triangle is narrow at the end 48 of the prong 37 at the end 38 of the inner tubular member 34. The triangle is wider at the opposing distal end 46 of the prong 37. As best shown in FIG. 6, the prongs 37 therefore have two elongated side edges 50, 52 and a short base edge 54 at the distal end 46 of the prong 37. As best shown in FIG. 8, the forceps hook 44 on the first pair of prongs 40 extends inwardly and perpendicularly from the short base edge 54. Preferably, forceps hook 44 is located at the extreme edge of base edge 54 adjacent one of the elongated side edges 50. In the preferred embodiment, each forceps hook 44 has a length L (FIG. 8) slightly in excess of the diameter D (FIG. 6) of inner cylindrical surface 36.

Figure 7:
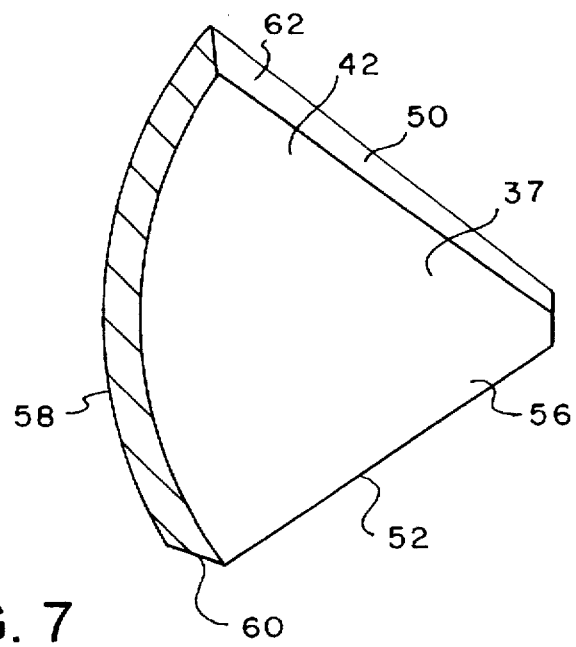
FIG. 7 is a sectional view taken along lines 7—7 of FIG. 6.
Figure 9:
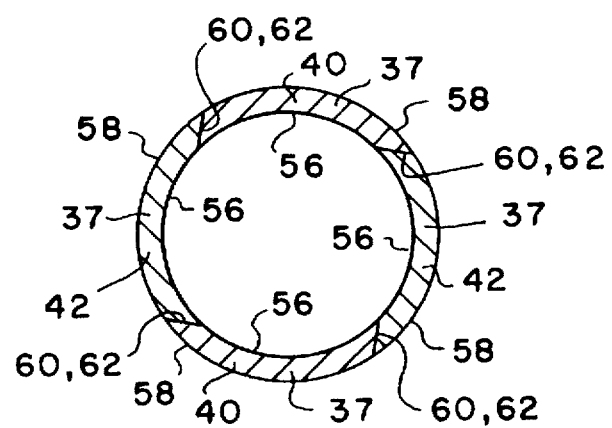
FIG. 9 is a sectional view taken along lines 9—9 of FIG. 4.

As best shown in FIGS. 7, 8, and 9, each prong 37 has an inner and outer concave surface 56, 58. Each outer concave surface has a degree of curvature approximately the same as the inner cylindrical surface 36 of the inner tubular member 32. Each inner cylindrical surface 56 is concentric with its corresponding outer cylindrical surface 58.

The elongated side edges 50, 52 are tapered inwardly at tapered surfaces 60, 62. As best shown in FIGS. 7–9, each tapered surface 50, 52 is on the opposite side of the prong 37, such that adjacent prongs imbricate as shown in FIG. 9 as the inner tubular member is drawn into the middle tubular member. The imbricating of the prongs 37, by way of the tapered edges, permits the prongs to capture and compress a stump of tubular tissue within the interleaved prongs as they are drawn into the inner cylindrical surface 36 of the middle tubular member. At that time, the band 12 can be perfectly positioned on the stump 18 (FIG. 2) in a precise and efficient manner.

As best shown in FIG. 6, in the preferred embodiment, an intermediate portion 64 of the prongs 37 has an included angle A with respect to the main axis 66 of the instrument of about 20 degrees, whereas an end portion 68 of each prong 37 has an included angle B with respect to axis 66 of about 15 degrees. In the preferred embodiment, the four prongs 37 are equally spaced about the axis 66 about ninety degrees apart.

Upon drawing in the prongs 37, each adjacent prong 37 rotates clockwise, giving an effect of clockwise rotation on the grasped tissue. The prongs slide along the inner cylindrical surface 36 as the gap between the prongs narrows and is finally obliterated. As the gap between the prongs 37 is obliterated, the prongs synchronously overlap each other as shown in FIG. 9. Thereby the stump is held securely with no bulging of grasped tissue between the prongs. The stump is easily banded at this point. There is no tissue vagrancy between the prongs because of the special overlapping and imbricating of the side edges of the prongs. In the preferred embodiment, the four prongs 37 are equally spaced about the axis 66 about ninety degrees apart.

In operation, the improved use of the applicator is enabled by the following features:

1. The two opposing forceps hooks at the distal ends of the first pair of prongs are in a straight line from the base edge of the prong, and the total length of the two hooks is a little more than the applicator's middle tubular member diameter.
2. The widening and concaving of the distal parts of the four prongs such that they curve around the stump tissue and enfold it securely.

With this improved instrument, Yoon-Banding an appendicular or meso-appendicular stump is a simple and precise procedure.

Whereas, the present invention has been described with the respect to a specific embodiment thereof, it will be understood that various changes and modifications will be suggested to one skilled in the art, and it is intended to encompass such changes and modifications as fall within the scope of the appended claims.

We claim:

1. A telescopic band applicator for use in applying an elastic band to a stump of tubular tissue, comprising:

an outer tubular member, a middle tubular member telescopically received within the outer tubular member and having an inner cylindrical surface, and an inner tubular member telescopically received within the middle tubular member;

and a plurality of partially cylindrical prongs at the end of the inner tubular member adapted and arranged to compress and capture the stump within the inner cylindrical surface of the middle tubular member.

2. The applicator of claim 1 the prongs being arranged as first and second opposed pairs of identical prongs.

3. The applicator of claim 2 with each of the first pair of prongs having an inwardly facing forceps hook at a distal end thereof.

4. The applicator of claim 1 with each prong being formed in the shape of an elongated triangle being narrower at the end of the inner tubular member and wider at the opposing distal end of the prong.

5. The applicator of claim 4 with each prong having two elongated side edges and a short base edge at the distal end, and a forceps hook on the end of each of the first pair of prongs extending inwardly and perpendicularly from the short base edge.

6. The applicator of claim 1 with each prong having inner and outer concave surfaces, each outer concave surface having a degree of curvature approximately the same as the inner cylindrical surface of the middle tubular member, and each inner cylindrical surface being concentric with the outer cylindrical surface of a prong.

7. The applicator of claim 1 with the prongs having a predetermined width and elongated side edges of the prongs being tapered inwardly such that adjacent prongs imbricate as the inner tubular member is drawn into the middle tubular member to capture and compress a stump of tubular tissue within the interleaved prongs and draw it into the middle tubular member.

8. A telescopic band applicator for use in applying an elastic band to a stump of tubular tissue, comprising:

an outer tubular member, a middle tubular member telescopically received within the outer tubular member and having an inner cylindrical surface, and an inner tubular member telescopically received within the middle tubular member;

four prongs attached to an end of the inner tubular member, the prongs being arranged as first and second opposed pairs of identical prongs, each of the first pair of prongs having an inwardly facing forceps hook at a distal end thereof, each prong being formed in the shape of an elongated triangle being narrower at the end of the inner tubular member and wider at the opposing distal end of the prong, with two elongated side edges and a short base edge at the distal end, the forceps hooks on the first pair of prongs extending inwardly and perpendicularly from the short base edge, and the forceps hooks having a length slightly in excess of the diameter of the middle tubular member inner cylindrical surface;

each prong having inner and outer concave surfaces, each outer concave surface having a degree of curvature approximately the same as the inner cylindrical surface of the middle tubular member, each inner cylindrical surface being concentric with the outer cylindrical surface of a prong; and the prongs having a predetermined width, and the elongated side edges of the prongs being tapered inwardly, such that adjacent prongs imbricate as the inner tubular member is drawn into the middle tubular member to capture and compress a stump of tubular tissue within the interleaved prongs and draw it into the inner cylindrical surface of the middle tubular member.

\* \* \* \* \*